(12) United States Patent
Jacquot et al.

(10) Patent No.: US 9,073,822 B2
(45) Date of Patent: Jul. 7, 2015

(54) PROCESS FOR PRODUCING COMPOUNDS COMPRISING NITRILE FUNCTIONS

(75) Inventors: Roland Jacquot, Francheville (FR); Philippe Marion, Vernaison (FR)

(73) Assignee: RHODIA OPERATIONS, Aubervilliers (FR)

( * ) Notice: Subject to any disclaimer, the term of this patent is extended or adjusted under 35 U.S.C. 154(b) by 161 days.

(21) Appl. No.: 13/699,237

(22) PCT Filed: May 17, 2011

(86) PCT No.: PCT/EP2011/057981
§ 371 (c)(1),
(2), (4) Date: Feb. 1, 2013

(87) PCT Pub. No.: WO2011/144619
PCT Pub. Date: Nov. 24, 2011

(65) Prior Publication Data
US 2013/0204001 A1    Aug. 8, 2013

(30) Foreign Application Priority Data

May 21, 2010 (FR) ...................................... 10 53967

(51) Int. Cl.
| | | |
|---|---|---|
| *C07C 69/34* | (2006.01) | |
| *C07C 255/00* | (2006.01) | |
| *C07C 253/30* | (2006.01) | |
| *C07C 253/00* | (2006.01) | |
| *C07C 67/20* | (2006.01) | |
| *C07C 209/48* | (2006.01) | |
| *C07D 207/408* | (2006.01) | |
| *C07D 211/88* | (2006.01) | |

(52) U.S. Cl.
CPC ............. *C07C 253/30* (2013.01); *C07C 253/00* (2013.01); *C07C 67/20* (2013.01); *C07C 209/48* (2013.01); *C07D 207/408* (2013.01); *C07D 211/88* (2013.01)

(58) Field of Classification Search
USPC .......................................... 560/190; 558/378
See application file for complete search history.

(56) References Cited

U.S. PATENT DOCUMENTS

| | | | |
|---|---|---|---|
| 2,444,828 A | 7/1948 | Kaplan | |
| 4,474,882 A | 10/1984 | Kunishige et al. | |
| 7,528,275 B2 * | 5/2009 | Bartsch et al. | ................ 558/332 |
| 2009/0326260 A1 | 12/2009 | Leconte et al. | |
| 2009/0326261 A1 | 12/2009 | Leconte et al. | |
| 2012/0071686 A1 | 3/2012 | Jacquot et al. | |

FOREIGN PATENT DOCUMENTS

| | | |
|---|---|---|
| CN | 101479229 A | 7/2009 |
| CN | 101528661 A | 9/2009 |
| EP | 0 471 566 A1 | 2/1992 |
| WO | 91/06660 A1 | 5/1991 |
| WO | 2008/009792 A1 | 1/2008 |
| WO | 2009/056477 A1 | 5/2009 |

OTHER PUBLICATIONS

Klein, J . Org. Chem., vol. 36, No. 20, 1971, 3050-3051.*
International Search Report issued on Aug. 1, 2011, by the European Patent Office as the International Searching Authority in International Patent Application No. PCT/EP2011/057981.
Laeckmann et al., "Synthesis and Biological Evaluation of Aroylguanidines Related to Amiloride as Inhibitors of the Human Platelet Na+/H+ Exchanger," Bioorganic & Medicinal Chemistry, 2002, p. 1793-1804, vol. 10.
Miller, "Succinimid," The Journal of the American Chemical Society, 1894, p. 432-462, vol. 16, No. 7.
Seldner, "Glutarimide," American Chemical Journal, 1985, p. 532-535, vol. 17.

* cited by examiner

*Primary Examiner* — Nizal Chandrakumar
(74) *Attorney, Agent, or Firm* — Dentons US LLP

(57) ABSTRACT

The production of compounds comprising nitrile functions and of cyclic imide compounds is described. Further described, is the production of compounds comprising nitrile functions from compounds comprising carboxylic functions, optionally of natural and renewable origin, and from a mixture N of dinitriles comprising 2-methylglutaronitrile (MGN), 2-ethylsuccinonitrile (ESN) and adiponitrile (AdN).

8 Claims, No Drawings

PROCESS FOR PRODUCING COMPOUNDS COMPRISING NITRILE FUNCTIONS

CROSS-REFERENCE TO PRIOR APPLICATIONS

This application is a National Stage of PCT/EP2011/057981, filed May 17, 2011, and designating the United States (published in French on Nov. 24, 2011, as WO 2011/144619 A1; the title and abstract were published in English), which claims priority to FR 10/53967, filed May 21, 2010, each hereby expressly incorporated by reference in its entirety and each assigned to the assignee hereof.

The present invention relates to the production of compounds comprising nitrile functions and of cyclic imide compounds.

It relates more particularly to the production of compounds comprising nitrile functions from compounds comprising carboxylic functions, advantageously of natural and renewable origin, and from a mixture N of dinitriles comprising 2-methylglutaronitrile (MGN), 2-ethylsuccinonitrile (ESN) and adiponitrile (AdN).

Compounds comprising nitrile functions are important products for the production of amine compounds. Dinitrile compounds give rise to amines which are, for example, monomers responsible for polymers such as polyamide, for example. Mononitrile compounds give rise to amines or to amides which are, for example, used for the production of cationic surfactants.

Many processes for synthesizing nitriles have been proposed, in particular processes for synthesis from ammonia and from carboxylic acids. These processes mainly use, as starting raw material, hydrocarbon compounds resulting from oil refining, and ammonia, which is obtained from hydrogen by steam reforming processes which consume a lot of energy.

Given that oil resources are running out, many research studies are undertaken in order to develop processes for synthesizing these compounds, which are important in the production of materials used in numerous applications, from raw materials and resources termed renewable, or from recycled raw materials, which are normally destroyed or exploited in the form of energy. These renewable resources are generally produced from cultivated or non-cultivated vegetable matter such as trees, plants such as sugarcane, corn, cassava, wheat, rapeseed, sunflower, palm, castor-oil plant or the like, or from animal matter such as fats (tallow, etc.).

This vegetable or animal matter is converted by means of processes generally comprising several mechanical, chemical and biological steps.

Moreover, with regard to recycled raw materials, the production of adiponitrile, a major chemical intermediate used in particular in the synthesis of hexamethylenediamine and caprolactam (monomers for the production polyamides), obtained by hydrocyanation of butadiene, generates a stream of dinitrile by-products comprising predominantly branched dinitrile compounds such as 2-methylglutaronitrile or 2-ethylsuccinonitrile. This mixture of branched dinitrile compounds is obtained by distillation in order to separate it from adiponitrile. Since the separation is not generally complete, the mixture of branched dinitrile compounds can also comprise a small proportion of adiponitrile.

Several solutions have been proposed for exploiting these by-products or mixtures. One of these consists in hydrogenating the dinitrile compounds to give primary amines in particular for producing 2-methylpentamethylenediamine (MPMD), used as a monomer for the production of particular polyamides or as an intermediate for the production of vitamin B3 (nicotinamide).

This process requires steps for purifying the 2-methylglutaronitrile and the 2-methylpentamethylenediamine.

Industrially, these by-products are also exploited in the form of vapour or energy by combustion. However, this combustion may require processing of the gases in order to remove the nitrogen oxides produced and it produces carbon dioxide which is discharged into the atmosphere There is therefore a need and a considerable requirement to find new routes for exploiting and converting these dinitrile compounds or mixtures to give chemical compounds which can be exploited and which are economically advantageous.

To this effect, the invention proposes a process for preparing at least one nitrile of general formula I

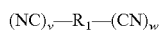

and at least the cyclic imides 3-methylglutarimide and 3-ethylsuccinimide, by reaction between at least one carboxylic acid of general formula II

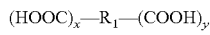

and a mixture N of dinitriles comprising 2-methylglutaronitrile (MGN), 2-ethylsuccinonitrile (ESN) and adiponitrile (AdN),
with
x, y is equal to 0 or 1 with (x+y) equal to 1 or 2
v, w is equal to 0 or 1 with (v+w) equal to 1 or 2
$R_1$ represents a linear or branched, saturated or unsaturated hydrocarbon-based group which may comprise heteroatoms, comprising:
  from 4 to 34 carbon atoms when (x+y) is equal to 2,
  from 2 to 22 carbon atoms when (x+y) is equal to 1.

Advantageously, the mixture N of dinitriles is a mixture resulting from the process for producing adiponitrile by double hydrocyanation of butadiene. It preferably corresponds to the distillation fraction which makes it possible to separate the branched dinitriles (2-methylglutaronitrile, 2-ethylsuccinonitrile) from adiponitrile.

This mixture of dinitriles generally has the following composition by weight:
  2-Methylglutaronitrile: between 70% and 95%, preferably between 80% and 85%,
  2-Ethylsuccinonitrile: between 5% and 30%, preferably between 8% and 12%,
  Adiponitrile: between 0% and 10%, preferably between 1% and 5%, the rest to 100% corresponding to various impurities.

The process of the invention uses a carboxylic acid of general formula II as described above.

The $R_1$ radical may be an aliphatic radical, or a group comprising an aromatic or cycloaliphatic radical, it may be functionalized, for example, with a hydroxyl function, an ester function, etc.

The compound of formula II may, for example, be chosen from trichloroacetic acid, trifluoroacetic acid, caproic acid, caprylic acid, pelargonic acid, capric acid, lauric acid, myristic acid, palmitic acid, stearic acid, arachidic acid, adipic acid, heptanedioic acid, octanedioic acid, azelaic acid, sebacic acid, or undecanedioic acid, dodecanedioic acid, brassylic acid, tetradecanedioic acid, hexadecanedioic acid, octadecanedioic acid, eicosanedioic acid, docosanedioic acid, octadecenoic acid, oleic acid, ricinoleic acid, erucic acid, linoleic acid, linolenic acid and fatty acid dimers containing 36 carbon atoms, terephthalic acid and isophthalic acid.

In the context of the process of the invention, a mixture of carboxylic acids of general formula II may be used. By way of example of a mixture of acids, mention may be made of coconut acids which result from palm oil or from coconut oil.

Advantageously, the carboxylic acid of general formula II is derived from a renewable matter of vegetable or animal origin.

A renewable matter or resource is a natural, animal or plant resource whose stock can be reconstituted over a short period on the human timescale. It is in particular necessary for this stock to be able to be renewed as quickly as it is consumed.

Unlike materials derived from fossil matter, renewable raw materials contain a large proportion of $^{14}C$. Preferably, the nitriles of the invention consist of organic carbon derived from renewable raw materials. Thus, this preferred characteristic could be guaranteed by determining the $^{14}C$ content according to one of the methods described in standard ASTM D6866, in particular according to the mass spectrometry method or the liquid scintillation spectrometry method which are described in this standard.

These renewable resources are generally produced from cultivated or non-cultivated vegetable matter such as trees, plants such as sugarcane, corn, cassava, wheat, rapeseed, sunflower, palm, castor-oil plant or the like, or from animal matter such as fats (tallow, etc.).

For example, the carboxylic acid of general formula II can be derived from renewable resources such as vegetable oils or natural polysaccharides such as starch or cellulose, it being possible for the starch to be extracted, for example, from corn or potato. It may in particular originate from various conversion processes, in particular conventional chemical processes, but also enzymatic conversion processes or fermentation conversion processes.

When the compound of formula II is a fatty monoacid, the latter can, for example be obtained from vegetable or animal oil by chemical conversion (hydrolysis of the oils).

When the compound of formula II is a diacid, the latter can be obtained by fermentation from a fatty monoacid obtained according to the method above. For example, it is possible to use the yeast *Candida tropicalis* modified in order to carry out the conversion of a monoacid to a diacid. Reference may particularly be made to documents WO 91/06660 and U.S. Pat. No. 4,474,882. The diacid can also be obtained from vegetable or animal oil by chemical conversion.

When the raw material is a polysaccharide, the compound of formula II is generally obtained by fermentation.

Advantageously, the compound of formula II is chosen from caproic acid, caprylic acid, pelargonic acid, capric acid, lauric acid, myristic acid, palmitic acid, stearic acid, arachidic acid, adipic acid, heptanedioic acid, octanedioic acid, azelaic acid, sebacic acid, or undecanedioic acid, dodecanedioic acid, brassylic acid, tetradecanedioic acid, hexadecanedioic acid, octadecanedioic acid, eicosanedioic acid, docosanedioic acid, octadecenoic acid, oleic acid, ricinoleic acid, erucic acid, linoleic acid, linolenic acid and fatty acid dimers containing 36 carbon atoms, and terephthalic acid.

The azelaic acid can be obtained from oleic acid, by ozonolysis.

The heptanedioic acid and the sebacic acid can be obtained from castor oil.

The dodecanedioic acid can be obtained by biofermentation of dodecanoic acid, also called lauric acid, it being possible for the lauric acid to be produced from coconut oil or from palm-kernel oil.

The brassylic acid can be obtained from erucic acid (in particular by ozonolysis), it being specified that erucic acid is in ester form in rapeseed.

The tetradecanedioic acid can be obtained by biofermentation of myristic acid, it being possible for the myristic acid to be produced from coconut oil or from palm-kernel oil.

The hexadecanedioic acid can be obtained by biofermentation of palmitic acid, the latter being contained mainly in palm oil.

The octadecanedioic acid can be obtained by biofermentation of steric acid, it being specified that stearic acid can be present in all vegetable oils, but especially in animal fats.

The eicosanedioic acid can be obtained by biofermentation of arachidic acid, which is found mainly in rapeseed oil.

The docosanedioic acid can be obtained by metasynthesis of undecylenic acid which is extracted from castor oil.

The aliphatic linear diacid having 36 carbon atoms is a fatty acid dimer derived, for example, from the by-products of resinous compounds converted by the Kraft processes. It can also be obtained by oligomerization or polymerization of unsaturated monobasic fatty acids comprising a long hydrocarbon-based chain (such as linoleic acid and oleic acid), as described in particular in document EP 0471566.

The process of the invention is advantageously carried out at a temperature of between 150 and 350° C. The pressure used is generally between atmospheric pressure and a few bar.

Catalysts can be used in the context of the process of the invention. By way of example of catalysts, mention may be made of phosphoric acid, phosphates, borophosphates, sulfuric acid, sulfonic acid, benzenesulfonic acid, toluenesulfonic acids such as para-toluenesulfonic acid, naphthalenesulfonic acids, silica, alumina, clay, and silica/alumina.

Advantageously, an amount of mixture N is used such that at least one molecule of 2-methylglutaronitrile (MGN) or of 2-ethylsuccinonitrile (ESN) is introduced into the reaction medium, per acid function of the carboxylic acid of general formula II to be converted into nitrile function.

When a diacid is used as acid of general formula II, it is possible to obtain the corresponding dinitrile or the corresponding acid nitrile (example, by using a nitrile function deficit).

During the reaction between the compound of formula (II) and the mixture N of dinitriles in accordance with the invention, imides are formed, in particular 3-methylglutarimide derived from MGN and 3-ethylsuccinimide derived from ESN.

Advantageously, the process of the invention also comprises a step of recovering, on the one hand, at least the nitrile of formula (I) and, on the other hand, at least the cyclic imide, from the reaction medium.

This recovery can be carried out by separation of the compounds from the reaction medium, according to any known method, such as distillation.

According to a first advantageous embodiment, the compounds can be obtained by reactive distillation. This is because, when the nitrile of formula (I) that it is desired to obtain has a boiling point below that of the reaction temperature (which is in particular the case for nitriles having a low carbon number), this nitrile can be distilled as it is formed, thereby shifting the equilibrium of the reaction toward the formation of this nitrile; this is therefore particularly advantageous. This reactive distillation method can, for example, be used when the nitrile of formula (I) is octanitrile or nonanitrile.

According to a second advantageous embodiment, the compounds can be separated by extraction with hot water. This is because imides are generally soluble in water, unlike, in particular, fatty nitriles, which allows good separation via a route that is easy to implement. This route is to be preferred in particular when the nitriles and the imides to be separated have boiling points which are close and when they are consequently difficult to separate by conventional distillation, for example. This method of extraction with hot water can, for example, be used when the nitrile of formula (I) is lauronitrile or oleonitrile or when a mixture of acids of formula (II) is used. The temperature of the water during this extraction is generally greater than or equal to 50° C.

According to one particular embodiment of the invention, the nitrile of formula (I) thus recovered is hydrogenated so as to form the corresponding amine, according to a method known to those skilled in the art. An amine of which all the carbons are bio-based (since they are derived from a bio-based carboxylic acid, i.e. a carboxylic acid derived from a renewable raw material) and of which the nitrogen atoms are recycled (since they are derived from by-products that are usually burned, thereby generating carbon dioxide and nitrogen oxides, which are greenhouse gases that must be processed in order to meet the legislation in force) is thus obtained. Such amines can be used as raw materials for the production of polyamide, which will thus be partially or completely bio-based depending on the acids used for the polymerization. These amines can also be used for preparing surfactants.

According to another particular embodiment of the invention, the cyclic imide recovered according to the process of the invention can be reacted with an alcohol so as to form the corresponding diester. Such a process is known and in particular described in document WO 2008/009792 and WO 2009/056477. The diesters can be used as solvents.

Other details and advantages of the invention will become more clearly apparent in the light of the examples given below.

EXAMPLES

Examples 1 to 4

Preparation of Dinitriles

Example 1

Sebacic Acid Nitrilation 930 g (8.6 mol) of a mixture of dinitriles (85% MGN, 12% ESN, 3% AdN by weight), which are by-products of adiponitrile synthesis, are introduced with stirring into a 2-liter reactor stirred with a mechanical stirrer and equipped with a reflux condenser, and then 8.5 g of 85% orthophosphoric acid are added. 809 g (4 mol) of bio-based sebacic acid are introduced, still with stirring. The reaction medium is then gradually heated to reflux, i.e. to approximately 285° C. These conditions are maintained for 4 hours and then the reaction mixture is cooled to ambient temperature. Next, the mixture of 3-methylglutarimide, 3-ethylsuccinimide and 2-methylglutaronitrile placed in excess is successively distilled at around 140° C. under 8 mmHg, ending with distillation of the sebaconitrile at 185° C. under 12 mmHg.

The respective yields of imide mixture and of sebaconitrile are 95% and 92%. In a second step, the imides are treated with an alcohol, and in particular methanol, so as to obtain a mixture of methyl diesters (methyl 2-methylglutarate and methyl 2-ethylsuccinate). The sebaconitrile is hydrogenated to the corresponding diamine according to the procedure described in example 2.

Example 2

Sebaconitrile Hydrogenation 50 g of 1,12-decanediamine and 50 g of water are introduced into a 750-ml autoclave equipped with a self-aspirating turbine. 10 g of Raney nickel doped with 2% by weight of Cr and basified with sodium hydroxide are introduced. The reactor is flushed with nitrogen and then twice with hydrogen, with 10 bar of pressure. Heating is carried out under a hydrogen pressure of 20 bar at 90° C. The sebaconitrile of example 1 is then introduced with a pump; 400 g of dinitrile are injected of the course of 4 hours. The reaction is exothermic. The temperature is kept constant by cooling. After the end of the injection, the mixture is left at 90° C. for 15 min under 20 bar of hydrogen. The mixture is brought back to ambient temperature and the reactor is flushed with nitrogen. The catalyst is filtered off and partially recycled. A catalyst deactivation of 1 g of nickel for 1 kg of hydrogenated dinitrile is accepted. The diamine is then purified by distillation under reduced pressure. The diamine is recovered at 140° C. under 10 mmHg, the latter solidifies at 62° C. The yield is 95%. In order to have a maximum reaction yield, it is necessary to supply the nitrile at a sufficient flow rate without accumulating the nitrile in the reaction medium.

Example 3

Terephthalic Acid Nitrilation 650 g (6.0 mol) of a mixture of dinitriles (85% MGN, 12% ESN, 3% AdN by weight) which are by-products of adiponitrile synthesis are introduced into a 2000-ml reactor. 167 g of terephthalic acid (1.0 mol) are added to this heterogeneous medium, followed by 5 g of 85% orthophosphoric acid. The reaction medium is heated at the reflux of the dinitriles and these conditions are maintained for 5 h. Respective yields of imide mixture and of 1,4-dicyanobenzene of 96% and 95% are obtained by GC analysis.

Example 4

Adipic Acid Nitrilation 146.3 g of adipic acid (1 mol) and 221 g (2.05 mol) of a mixture of dinitriles (85% MGN, 12% ESN, 3% AdN by weight) which are by-products of adiponitrile synthesis are introduced into a 500-ml reactor. 2.0 g of 85% orthophosphoric acid are added to the yellowish suspension and the medium is heated with stirring at reflux. These conditions are maintained for 3 hours. The following results are obtained by GC analysis:
94% conversion of the dinitrile mixture
95% imide mixture yield
75% adiponitrile yield.

Examples 5 to 11

Preparation of Mononitriles

Example 5

Pelargonic Acid Nitrilation 930 g (8.6 mol) of a mixture of dinitriles (85% MGN, 12% ESN, 3% AdN by weight) which are by-products of adiponitrile synthesis are introduced into a 2-liter reactor equipped with a mechanical stirrer and with a reflux condenser. 8.0 g of 85% orthophosphoric acid are added. Stirring is carried out and 1265 g (8.0 mol) of bio-based pelrgonic acid are introduced. The reaction medium is gradually heated to the reflux of pelargonic acid, i.e. about 269° C. The nonanenitrile, which has a lower boiling point (224° C.), is then gradually distilled and, as a result, the equilibrium of the reaction is shifted. After heating for 6 hours, the nitrile is recovered with a yield of 95% relative to the pelargonic acid used. The MGN placed in excess is then distilled, as are the imides which can be used in the esterification reaction with methanol.

Example 6

Nonanenitrile Hydrogenation 50 g of nonylamine and 50 g of water are introduced into a 750-ml autoclave equipped with a self-aspirating turbine. 5 g of basified Raney nickel doped with 2% by weight of Cr are added. The reactor is flushed with twice 10 bar of nitrogen and then with twice 10 bar of hydrogen. The autoclave is placed under 20 bar of hydrogen, and stirring and heating to 90° C. are carried out. The nonanenitrile resulting from example 5 is then injected using a pump, while keeping the hydrogen pressure constant in the reactor. 350 g of nonanenitrile are injected over the course of 4 h. After the end of the injection, the reaction medium is maintained under the same conditions for 30 min. The temperature is then brought back to 20° C., the reactor is flushed with nitrogen and the catalyst is filtered off. The reaction medium is then distilled under reduced pressure: in this way, the nonylamine is recovered with a yield of 98% (boiling point 201° C. under 760 mmHg).

Example 7

Oleic Acid Nitrilation 250 g (2.30 mol) of a mixture of dinitriles (85% MGN, 12% ESN, 3% AdN by weight) which are by-products of adiponitrile synthesis are introduced into a 2000-ml reactor equipped with stirring and with a reflux condenser, and 564 g (2 mol) of bio-based oleic acid are then added with stirring. 5.0 g of catalyst—orthophosphoric acid—at 85% are then run in. Heating is then carried out, still with stirring, at the reflux of the dinitrile mixture at 270-275° C. These conditions are maintained for 4 h. By GC analysis, an oleic acid conversion of 98% and an overall imide yield of 97% are obtained. The oleonitrile yield is 94%. The reaction medium is then washed at 65° C. with 3 times 250 g of water in order to remove from the medium the imides formed. Using this technique, the oleonitrile is recovered with a purity of 97%.

Example 8

Oleic Acid Nitrilation

The process is carried out in the same way as in example 7, but without adding catalyst. Under these conditions, the reflux is maintained for 6 h and an oleic acid conversion of 97% and an overall imide yield of 97% are obtained. The oleonitrile yield is 95%. The reaction medium can also be treated with water at 65° C., as in example 7, in order to separate the imides and the oleonitrile.

Example 9

Monomethyl Azelate Nitrilation 40.5 g of bio-based azelaic acid monomethyl ester and 21.6 g (0.2 mol) of a mixture of dinitriles (85% MGN, 12% ESN, 3% AdN by weight) which are by-products of adiponitrile synthesis are introduced into a 250-ml reactor equipped with a mechanical stirrer. 0.2 g of 85% orthophosphoric acid is added to the solution obtained, while stirring. The mixture is heated at reflux, i.e. at approximately 270° C. After maintaining these conditions for 3 hours, the azelaic acid monomethyl ester conversion is complete and the imine mixture yield is 91%. The azelaic acid cyanoester yield is 85%.

Example 10

Sebacic Acid Mononitrilation 202 g (1.0 mol) of bio-based sebacic acid and 108 g (1.0 mol) of a mixture of dinitriles (85% MGN, 12% ESN, 3% AdN by weight) which are by-products of adiponitrile synthesis are introduced into a 500-ml reactor equipped with a mechanical stirrer and heated using an electrical heating mantle. The mixture is stirred and heated, and when it is homogeneous, 0.4 g of 85% orthophosphoric acid is then added. The temperature of the medium is brought to reflux, i.e. to a temperature close to 270° C. These conditions are maintained for 4 hours. After this time, a 65% yield of the corresponding nitrile acid and a 90% yield of imide mixture corresponding to the dinitrile mixture are obtained.

Example 11

Lauric Acid Nitrilation 80 g (400 mmol) of bio-based lauric acid and 48 g (440 mmol) of a mixture of dinitriles (85% MGN, 12% ESN, 3% AdN by weight) which are by-products of adiponitrile synthesis are introduced into a 250-ml reactor equipped with a mechanical stirrer and heated using an electrical heating mantle. The reaction medium is stirred and heated in order to homogenize it, and 0.4 g of 85% orthophosphoric acid is added. The resulting mixture is then heated at reflux at about 270° C., and these conditions are maintained for 3 hours. The temperature of the medium is then brought back to about 95° C., and 50 g of water are added. The medium is stirred for 15 min at 60° C. and separated by setting out in order to recover the imides and partially the dinitriles placed in excess in aqueous solution. The organic phase which contains the lauronitrile is extracted twice more with a further 50 g of water still at 65° C. The lauronitrile is then recovered with a yield of 92% and a purity of 93%.

Example 12

Octanoic Acid Nitrilation 594 g (5.44 mol) of a mixture of dinitriles (85% MGN, 12% ESN, 3% AdN by weight) which are by-products of adiponitrile synthesis are introduced into a 2000-ml reactor equipped with a stirrer and with a continuous distillation device. 751 g (5.15 mol) of octanoic acid are added. 1.3 g of 85% orthophosphoric acid are added, with stirring. The reaction medium is heated, and becomes homogeneous at about 230-240° C. At this temperature, the octanitrile continuously distills as soon as it is formed. After 5 hours of reaction, 55 g of octanitrile are obtained, which represents a yield of 84%.

The invention claimed is:
1. A process for preparing at least one nitrile of general formula I

$$(NC)_v-R_1-(CN)_w \qquad (I)$$

and at least cyclic imides 3-methylglutarimide and 3-ethylsuccinimide, by reacting at least one carboxylic acid of general formula II $$(HOOC)_x—R_1—(COOH)_y \quad (II)$$

and a mixture N of dinitriles comprising 2-methylglutaronitrile (MGN), 2-ethylsuccinonitrile (ESN) and adiponitrile (AdN), wherein x, y are equal to 0 or 1 with (x+y) equal to 1 or 2, v, w are equal to 0 or 1 with (v+w) equal to 1 or 2, and $R_1$ represents a linear or branched, saturated or unsaturated hydrocarbon-based group which can comprise heteroatoms, comprising:

from 4 carbon atoms to 34 carbon atoms when (x+y) is equal to 2, and from 2 carbon atoms to 22 carbon atoms when (x+y) is equal to 1, and wherein the mixtures of dinitriles has the following composition by weight 2-Methylglutaronitrile from 80% to 85%, 2-Ethylsuccinonitrile from 8% to 12%, and Adiponitrile from 1% to 5%.

2. The process as defined in claim 1, wherein the mixture N of dinitriles is a mixture resulting from the process for producing adiponitrile by double hydrocyanation of butadiene.

3. The process as defined in claim 1, wherein the compound of formula II is derived from a renewable matter of vegetable or animal origin.

4. The process as defined in claim 3, wherein the compound of formula II is selected from the group consisting of a caproic acid, a caprylic acid, a pelargonic acid, a capric acid, a lauric acid, a myristic acid, a palmitic acid, a stearic acid, an arachidic acid, an adipic acid, a heptanedioic acid, an octanedioic acid, an azelaic acid, a sebacic acid, an undecanedioic acid, a dodecanedioic acid, a brassylic acid, a tetradecanedioic acid, a hexadecanedioic acid, an octadecanedioic acid, an eicosanedioic acid, a docosanedioic acid, an octadecenoic acid, an oleic acid, a ricinoleic acid, an erucic acid, a linoleic acid, a linolenic acid and a fatty acid dimer having 36 carbon atoms, and a terephthalic acid.

5. The process as defined in claim 1, wherein the process comprises recovering the at least one nitrile and the cyclic imides 3-methylglutarimide and 3-ethylsuccinimide by separation of the compound from the reaction medium.

6. The process as defined in claim 5, wherein the recovered nitrile is hydrogenated so as to form the corresponding amine.

7. The process as defined in claim 5, wherein the recovered cyclic imides 3-methylglutarimide and 3-ethylsuccinimide are reacted with an alcohol so as to form the corresponding diester.

8. The process as defined in claim 1, wherein the process comprises recovering the cyclic imides 3-methylglutarimide and 3-ethylsuccinimide by separating the compounds from the reaction medium.

\* \* \* \* \*